United States Patent [19]

Zurflüh

[11] 4,413,010

[45] Nov. 1, 1983

[54] CARBAMIC ACID ESTERS AND USE AS PESTICIDES

[75] Inventor: Rene Zurflüh, Bülach, Switzerland

[73] Assignee: Hoffmann-La Roche Inc., Nutley, N.J.

[21] Appl. No.: 301,612

[22] Filed: Sep. 14, 1981

[30] Foreign Application Priority Data

Sep. 23, 1980 [CH] Switzerland ............... 7120/80
Jun. 30, 1981 [CH] Switzerland ............... 4307/81

[51] Int. Cl.³ .................. A01N 47/10; C07C 125/06
[52] U.S. Cl. ..................... 424/300; 260/455 A; 560/27; 560/21
[58] Field of Search ........... 560/27, 21; 260/455 A; 424/286, 300

[56] References Cited

U.S. PATENT DOCUMENTS 4,215,139 7/1980 Fischer et al. ............... 560/27

Primary Examiner—Bernard Helfin

Attorney, Agent, or Firm—Jon S. Saxe; George M. Gould; John J. Maitner

[57] ABSTRACT

Carbamic acid compounds of the formula

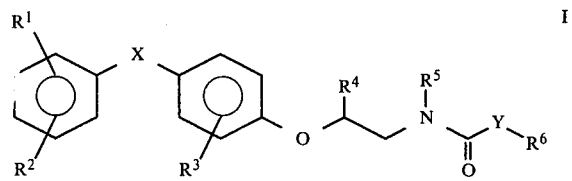

wherein $R^1$, $R^2$, $R^3$, $R^4$, $R^5$, $R^6$, X and Y are as hereinafter set forth, processes for their preparation, pesticidal compositions containing one or more of the carbamic acid compounds as the active ingredient and methods for using the pesticidal compositions for the control of pests, particularly insects, mites and nematodes, are described.

6 Claims, No Drawings

CARBAMIC ACID ESTERS AND USE AS PESTICIDES

DETAILED DESCRIPTION OF THE INVENTION

The invention is directed to carbamic acid derivatives of the general formula

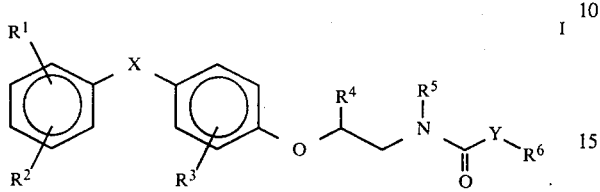

wherein $R^1$ is hydrogen, halogen, methyl, ethyl, trifluoromethyl or nitro; $R^2$ is hydrogen, halogen, methyl or trifluoromethyl; $R^3$ is hydrogen, halogen or methyl; $R^4$ is hydrogen or methyl; $R^5$ is hydrogen or $C_{1-4}$-alkyl, whereby both symbols $R^4$ and $R^5$ are not simultaneously hydrogen; $R^6$ is $C_{1-4}$-alkyl; X is oxygen, methylene or carbonyl; and Y is oxygen or sulfur.

This invention is also directed to compositions effective for pest control and especially for the control of insects, mites and nematodes, which contain, as the active component, one or more compounds of formula I. Finally, this invention is directed to processes for the preparation of such compositions.

As used herein, the term "halogen" denotes fluorine, chlorine, bromine and iodine. The term "$C_{1-4}$-alkyl" denotes not only straight-chain but also branched-chain alkyl groups such as methyl, ethyl, n-propyl, isopropyl, n-butyl, isobutyl and tert.butyl.

Since the compounds of formula I can contain asymmetric carbon atoms, these compounds can exist as optical antipodes. Formula I is accordingly intended to include these possible isomeric forms as well as the racemates.

If $R^1$ or $R^3$ is halogen, this is preferably fluorine, chlorine or bromine. If $R^2$ is halogen, then this is preferably fluorine or chlorine.

If $R^5$ is $C_{1-4}$-alkyl, then this is preferably methyl or ethyl.

$R^1$ preferably is hydrogen, halogen, methyl or trifluoromethyl.

$R^2$ preferably is hydrogen or halogen.

$R^3$ preferably is hydrogen.

$R^5$ preferably is hydrogen, methyl or ethyl.

$R^6$ preferably is methyl, ethyl, isopropyl or isobutyl.

X preferably is oxygen or methylene.

Preferred compounds of formula I are:
Ethyl [2-(p-phenoxyphenoxy)ethyl]ethylcarbamate,
ethyl 2-(p-phenoxyphenoxy)propylcarbamate,
ethyl [2-(p-phenoxy-m-tolyloxy)ethyl]methylcarbamate,
methyl [2-(p-phenoxyphenoxy)ethyl]methylcarbamate,
isopropyl [2-(p-phenoxyphenoxy)ethyl]methylcarbamate,
S-ethyl [2-(p-phenoxyphenoxy)ethyl]methylthiocarbamate,
ethyl {2-[p-(m-chlorophenoxy)phenoxy]ethyl}methylcarbamate,
ethyl {2-[p-(m-bromophenoxy)phenoxy]ethyl}methylcarbamate,
ethyl 2-(p-benzylphenoxy)propylcarbamate,
ethyl 2-[p-(m-fluorophenoxy)phenoxy]propylcarbamate, and
ethyl {2-[p-(m-fluorophenoxy)phenoxy]ethyl}methylcarbamate.

Especially preferred compounds of formula I are:
ethyl {2-[p-(p-fluorophenoxy)phenoxy]ethyl}methylcarbamate,
ethyl [2-(p-phenoxyphenoxy)ethyl]methylcarbamate,
ethyl {2-[p-(3,5-dichlorophenoxy)phenoxy]ethyl}methylcarbamate, and
ethyl 2-[p-(p-fluorophenoxy)phenoxy]propylcarbamate.

The compounds of formula I of this invention are prepared by the processes described below.

Procedure A

Reacting a phenol of the formula

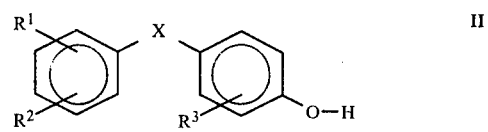

wherein $R^1$, $R^2$, $R^3$ and X are as defined hereinabove, with a compound of the formula

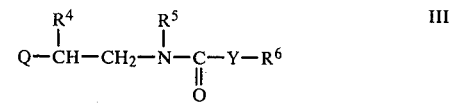

wherein $R^4$, $R^5$, $R^6$ and Y are as defined hereinabove and Q is a leaving group, especially chlorine, bromine, iodine, mesyloxy or tosyloxy.

A starting material of formula II is reacted with a compound of formula III conveniently in an inert organic solvent and in the presence of an acid-binding agent. Representative inert organic solvents include dimethylformamide, dioxan, hexamethylphosphoric acid triamide, tetrahydrofuran, dimethoxyethane, toluene and combinations of two or more of these solvents. Preferred acid-binding agents are alkali metals, especially sodium and potassium, alkali metal hydrides, alkali metal amides, alkali metal hydroxides and alkali metal carbonates, especially potassium carbonate. In this case, the corresponding alkali metal phenolate is formed from the phenol of formula II. Alternatively, the phenolate is formed from the phenol in the presence of an alkali metal hydroxide by azeotropically removing the resulting water with toluene.

The reaction temperature can vary over a wide range. In general, the reaction is carried out at a temperature between −20° C. and the boiling point of the reaction mixture, preferably between room temperature and 100° C., especially between 80° C. and 100° C. When the leaving group Q in formula III is bromine or iodine, the reaction temperatures are preferably somewhat lower than those when a compound of formula III in which the leaving group Q is chlorine, mesyloxy or tosyloxy is used.

The isolation of compounds of formula I is carried out using standard procedures.

Procedure B

Reacting an amine of the formula

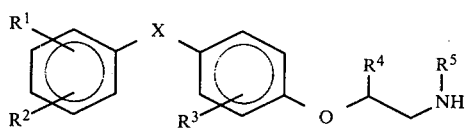

wherein $R^1$, $R^2$, $R^3$, $R^4$, $R^5$ and X are as defined hereinabove, with a compound of the formula

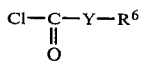

wherein $R^6$ and Y are as defined hereinabove, conveniently in the presence of an inert organic solvent and an acid-binding agent.

Representative inert organic solvents include acetone and methylene chloride. The reaction is preferably carried out in the presence of an acid-binding agent such as, for example, an alkali metal carbonate, preferably potassium carbonate. The reaction is preferably carried out at the reflux temperature of the reaction mixture. In general, the reaction is finished within one day. Thereafter, undissolved salts which may be present are conveniently filtered off from the reaction mixture and the filtrate is evaporated in vacuo. The residue is purified, for example by column chromatography, distillation or crystallization.

Insofar as no planned synthesis for the isolation of pure isomers is carried out, a product is normally obtained as a mixture of two isomers. The isomers can be separated employing standard procedures.

The starting materials of formulae II, III, IV and V are known or can be prepared according to known methods.

The compounds of formula I of this invention are active as pesticides and are especially valuable in the control of insects, mites and nematodes. They are especially valuable against: Lepidoptera such as, for example, Adoxophyes spp., *Tortrix viridana, Cheimatobia brumata, Lyonetia clerkella, Operophthera brumata, Lithocelletis blancardella*, and other boring moths, Laspeyresia spp., *Porthetria dispar*, Orgyia spp., Choristoneura spp., *Clysia ambiguella, Lobesia botraña, Agrotis segetum*, Heliothis spp., Spodoptera spp., *Ostrinia nubilalis*, Ephestia spp., *Galleria mellonella, Plodia interpunctella*.

Homoptera, i.e., shield and soft lice such as, for example, Aspidiotus spp., Saissetia spp., *Quadraspidiotus perniciosus, Aonidella aurantii*, Coccus spp., Unaspis spp., Lecania spp., as well as Lepidosaphes spp., Planococcus spp., Pseudococcus spp., Ceroplastes spp., *Icerya purchasi*, chrysomphalus spp., Parlatoria spp., Rhizoecus spp., as well as cicada such as, for example, Nephotettix spp., Laodelphax spp., Nilaparvata spp., as well as leaf suckers such as, for example, *Psylla mali, Psylla piri, Psylla pirisuga, Psylla piricula, Trioza apicalis*, aphids such as, for example, Aphis fabae, Myzus persicae, as well as white flies such as, for example, *Trialeurodes vaporariorum, Aleurodes proletella, Bemisia tabaci*.

Diptera such as, for example, Aedes aegypti, *Culex pipiens, Aedes taeniorrhynchus, Anopheles stephensi*, Calliphora spp., *Musca domestica*, Sciara spp., Phorbia spp., mushroom flies.

Coleoptera such as, for example, *Oryzaephilus surinamensis, Rhizopertha dominica, Sitophilus granarius, Sitophilus oryzae, Tenebrio molitor, Tribolium castaneum, Trogoderma granarium, Lasioderma serriorne*, Epilachna spp., Leptinotarsa spp., *Otiorhynchus sulcatus*, Diabrotica spp., and other soil Coleoptera.

Orthoptera such as, for example, *Blattella germanica, Leucophaea surinamensis, Nauphoeta cinerea, Blatta orientalis, Periplaneta americana*.

Heteroptera such as, for example, *Dysdercus cingulatus, Rhodnius prolixus, Oncopeltus fasciatus*, Piesma spp., Lygus spp.

Isoptera (termite species)

Hymenoptera such as, for example, *Solenopsis invicta, Monomorium pharaonis*, Atta spp., as well as true sawflies such as, for example, *Athalia rosae*, Hoplocampa spp., Pristiphora spp.

Acarina such as, for example, *Tetranychus urticae, Tetranychus cinnabarinus, Panonychus ulmi* and other Tetranychida, Eriophyida such as *Phyllocoptruta oleivora*, and, in addition, especially ticks.

Nematoda such as, for example, *Ditylenchus dipsaci, Meliodogyne incognita, Pratylenchus penetrans, Aphelenchoides rizemabosi* and *Globodera rostochiensis*.

The compounds of formula I of this invention act as contact or feed poisons and are also effective in the vapor phase. In contrast to most of the hitherto known pest control agents, which act as toxins on the nervous system of the animals and thereby kill, cripple or repel them, the compounds of formula I of this invention interfere with the hormonal system of the animal organism. In the case of insects, for example, the metamorphosis to the imago, the laying of viable eggs and the development of laid normal eggs is disturbed. Moreover, in various insect species the larval moultings are disturbed. The sequence of generations is interrupted and the animals are indirectly killed.

The compounds of formula I are practically non-poisonous to vertebrates since the toxicity is above 1000 mg/kg body weight. The compounds of formula I are also readily degraded and the danger of accumulation is therefore extruded. Therefore, they can accordingly be used for the control of pests on animals, plants, provisions and materials and in water.

The instant invention is also directed to pesticidal compositions such as solutions, emulsions, suspensions, powders, pastes and granulates which contain inert carrier materials and, as the active ingredient, one or more of the compounds of formula I.

These compositions are prepared by known methods such as, for example, by mixing the active substance with extenders (liquid solvents, liquified gases under pressure and/or solid carrier substances) and, if desired, surface-active agents (emulsifiers, wetting agents or dispersing agents). When water is used as the extender, organic solvents can also be used as auxiliary solvents.

Examples of liquid solvents include: aromatics such as xylenes, toluene and alkylnaphthalenes; chlorinated aromatics and chlorinated aliphatic hydrocarbons such as chlorobenzenes, chloroethylenes and methylene chloride; aliphatic hydrocarbons such as cyclohexane and paraffins (e.g., petroleum fractions); alcohols such as butanol and glycol as well as their ethers and esters; ketones such as acetone, methyl ethyl ketone, methyl isobutyl ketone and cyclohexanone; strongly polar solvents such as dimethylformamide, N-methylpyrrolidone and dimethylsulfoxide, and water.

Examples of liquified gaseous extenders or carrier substances include liquids which are gaseous at normal temperature and under normal pressure such as aerosol propellants, e.g., halogenated hydrocarbons (e.g., dichlorodifluoromethane).

Examples of solid carrier substances include natural mineral substances such as kaolins, clays, talc, chalk, quartz, attapulgite, montmorillonite and diastomaceous earth, and synthetic mineral substances such as high-dispersible silicic acid, aluminum oxide and silicates.

Surface-active agents, especially emulsifying agents and wetting agents, suitable for use in the pesticidal compositions of this invention can be non-ionic or anionic. Examples of non-ionic emulsifiers which can be used include polyoxyethylene-fatty acid esters, polyoxyethylene-fatty alcohol ethers and alkylaryl-polyglycol ethers. Examples of anionic emulsifiers include alkyl sulfonates, alkyl sulfates and aryl sulfonates.

Examples of dispersing agents include lignin, sulfite lyes and methyl cellulose.

The compositions generally contain between 0.0005 weight percent and 95 weight percent of compound or compounds of formula I as active ingredient, preferably between 1 weight percent and 75 weight percent.

The pesticidal compositions of the present invention can be in application forms suitable for storage or shipment. In such forms (e.g., emulsifiable concentrates), the concentration of active ingredients is normally at the higher end of the above concentration range. These forms can then be diluted with the same or different carrier materials to afford active ingredient concentrations suitable for practical use, and such concentrations normally lie at the lower end of the above-noted concentration range. Emulsifiable concentrates generally contain 5 to 95 weight percent, preferably 10 to 75 weight percent, of the compound or compounds of formula I.

The active ingredients can also be used as such in the compositions or in application forms prepared from these compositions such as ready-for-use solutions, emulsions, foams, suspensions, powders, pastes, soluble powders, dusting agents and granulates. They are used in the usual procedures such as sprinkling, spraying, smokescreening, dusting, scattering, drilling-in, vaporizing, pouring, drenching or incrustating.

The concentrations of active ingredient in the ready-for-use preparations can vary over wide limits. In spray liquors, the concentration lies between 0.0005 weight percent and 20 weight percent.

The active ingredients can also be used with good effect in the ultra-low-volume process (ULV) where it is possible to formulate spray liquors having preferably from 0.5 to 20 weight percent.

The active ingredients can also be used with good effect in the low-volume process and in the high-volume process where it is possible to formulate spray liquors having from 0.02 to 1.0 or 0.002 to 0.1 weight percent of active ingredient respectively.

In granulates, which are used especially in mosquito control, the concentration of active ingredients is preferably from 1 to 10 weight percent of the compound or compounds of formula I as the active substance.

The pesticidal compositions of the present invention can contain other active substances, for example, other pesticides, besides the compounds of formula I. Such combination compositions are suitable for increasing the activity or for broadening the spectrum of activity.

In preparing the pesticidal compositions of the present invention, the active ingredient of formula I is mixed with inert carrier material. In the case of pulverous compositions, the active ingredient can be mixed with the carrier substances, for example, by milling together; or the inert carrier material can be impregnated with a solution or suspension of the active ingredient and then the solvent or suspension agent can be removed by evaporation, heating or by filtering under reduced pressure. By the addition of wetting and/or dispersing agents such pulverous compositions can be made readily wettable with water so that they can be converted into aqueous suspensions which are suitable, for example, as spray compositions. For the manufacture of emulsifiable concentrates, which are especially suitable for storage and shipment, the active ingredient can be mixed, for example, with an emulsifying agent or dissolved in an inert solvent and thereafter mixed with an emulsifier. Ready-for-use emulsions are prepared by diluting such concentrates with water.

The pesticidal compositions of the present invention are used by treating the locus to be protected or the pests themselves with a compound of this invention or with the pesticidal compositions of the present invention. This method of use is preferably carried out by applying the composition to the soil or leaves, or by application to the animals, provisions or materials to be protected, depending on the pests to be controlled. The control is achieved, for example, by contact or by intake with food.

In addition to their pesticidal properties, the compounds of formula I of this invention exhibit properties which produce an improvement in the quality of the silk thread in sericulture. Therefore, the compounds of formula I can be used in sericulture as additives to the feed of silkworms.

The following Examples illustrate the present invention:

I. Preparation of the active substances

EXAMPLE 1

18.6 g of p-phenoxyphenol are dissolved in 100 ml of dimethylformamide. 18.2 g of ethyl (2-chloroethyl)-methylcarbamate and 27.6 g of potassium carbonate are added thereto and the reaction mixture is heated at 80° C. while stirring for 15 hours. The reaction mixture is poured into 300 ml of water and extracted with diethyl ether. The ether extract is washed with semi-saturated and saturated sodium chloride solution, dried over sodium sulfate and evaporated. Chromatography on silica gel using n-hexane/ethyl acetate (9:1) as the eluent yields ethyl [2-(p-phenoxyphenoxy)ethyl]methylcarbamate; $n_D^{20} = 1.5503$.

Compounds of formula I are prepared from appropriate starting materials according to the procedure described above:

(1) p-(p-fluorophenoxy)phenol and ethyl (2-chloroethyl)methylcarbamate yield ethyl [2-[p-(p-fluorophenoxy)phenoxy]ethyl]methylcarbamate; $n_D^{20} = 1.5373$;

(2) p-benzylphenol and ethyl (2-chloroethyl)methylcarbamate yield ethyl [2-(p-benzylphenoxy)ethyl]methylcarbamate; $n_D^{20} = 1.5495$;

(3) p-phenoxyphenol and ethyl (2-chloroethyl)ethylcarbamate yield ethyl [2-(p-phenoxyphenoxy)ethyl]ethylcarbamate; $n_D^{20} = 1.5446$;

(4) p-phenoxyphenol and ethyl (2-chloroethyl)isopropylcarbamate yield ethyl [2-(p-phenoxyphenoxy)ethyl]isopropylcarbamate; $n_D^{20} = 1.5415$;

(5) p-phenoxyphenol and ethyl (2-chloroethyl)-n-butylcarbamate yield ethyl [2-(p-phenoxyphenoxy)ethyl]-n-butylcarbamate; $n_D^{20} = 1.5358$;

(6) p-(m-bromophenoxy)phenol and ethyl (2-chloroethyl)methylcarbamate yield ethyl [2-[p-(m-bromophenoxy)phenoxy]ethyl]methylcarbamate; $n_D^{20} = 1.5672$;

(7) p-phenoxyphenol and ethyl 2-(methylsulphonyloxy)propylcarbamate yield ethyl 2-(p-phenoxyphenoxy)propylcarbamate; m.p. 79°–81° C.;

(8) p-(m-bromophenoxy)phenol and ethyl 2-(methylsulphonyloxy)propylcarbamate yield ethyl 2-[p-(m-bromophenoxy)phenoxy]propylcarbamate; $n_D^{20} = 1.5660$;

(9) p-(m-fluorophenoxy)phenol and ethyl (2-chloroethyl)methylcarbamate yield ethyl [2-[p-(m-fluorophenoxy)phenoxy ethyl]methylcarbamate; $n_D^{20} = 1.5386$;

(10) p-(4-chloro-o-tolyloxy)phenol and ethyl (2-chloroethyl)methylcarbamate yield ethyl [2-[p-(p-chloro-o-tolyloxy)phenoxy]ethyl]methylcarbamate; $n_D^{20} = 1.5537$;

(11) p-phenoxy-m-cresol and ethyl (2-chloroethyl)methylcarbamate yield ethyl [2-(p-phenoxy-m-tolyloxy)ethyl]methylcarbamate; $n_D^{20} = 1.546$;

(12) p-phenoxyphenol and methyl (2-chloroethyl)methylcarbamate yield methyl [2-(p-phenoxyphenoxy)ethyl]methylcarbamate; $n_D^{20} = 1.5578$;

(13) p-phenoxyphenol and isopropyl (2-chloroethyl)methylcarbamate yield isopropyl [2-(p-phenoxyphenoxy)ethyl]methylcarbamate; $n_D^{20} = 1.5388$;

(14) p-phenoxyphenol and methyl 2-(methylsulphonyloxy)propylcarbamate yield methyl 2-(p-phenoxyphenoxy)propylcarbamate; $n_D^{20} = 1.5565$;

(15) p-phenoxyphenol and isopropyl 2-(methylsulphonyloxy)propylcarbamate yield isopropyl 2-(p-phenoxyphenoxy)propylcarbamate; $n_D^{20} = 1.5422$;

(16) p-(3,5-dichlorophenoxy)phenol and ethyl (2-chloroethyl)methylcarbamate yield ethyl [2-[p-(3,5-dichlorophenoxy)phenoxy]ethyl]methylcarbamate; $n_D^{20} = 1.5632$;

(17) P-(α,α,α-trifluoro-m-tolyloxy)phenol and isopropyl (2-chloroethyl)methylcarbamate yield isopropyl [2-[p-(α,α,α-trifluoro-m-tolyloxy)phenoxy]ethyl]methylcarbamate; $n_D^{20} = 1.5092$;

(18) p-(m-tolyloxy)phenol and ethyl (2-chloroethyl)methylcarbamate yield ethyl [2-[p-(m-tolyloxy)phenoxy]ethyl]methylcarbamate; $n_D^{20} = 1.5485$;

(19) p-(nitrophenoxy)phenol and ethyl (2-chloroethyl)methylcarbamate yield ethyl [2-[p-(p-nitrophenoxy)phenoxy]ethyl]methylcarbamate; $n_D^{20} = 1.5773$;

(20) 4-hydroxy-benzophenone and isopropyl (2-chloroethyl)methylcarbamate yield isopropyl [2-(p-benzoylphenoxy)ethyl]methylcarbamate; $n_D^{20} = 1.5608$;

(21) p-(p-fluorobenzoyl)phenol and ethyl 2-(methylsulphonyloxy)propylcarbamate yield ethyl 2-[p-(p-fluorobenzoyl)phenoxy]propylcarbamate; $n_D^{20} = 1.5682$;

(22) p-(m-bromophenoxy)phenol and isopropyl 2-(methylsulphonyloxy)propylcarbamate yield isopropyl [2-[p-(m-bromophenoxy)phenoxy]propylcarbamate; $n_D^{20} = 1.5590$;

(23) p-phenoxyphenol and S-ethyl (2-chloroethyl)methylthiocarbamate yield S-ethyl [2-(p-phenoxyphenoxy)ethyl]methylthiocarbamate; m.p. 28°–32° C.;

(24) p-(m-chlorophenoxy)phenol and ethyl 2-(methylsulphonyloxy)propylcarbamate yield ethyl 2-[p-(m-chlorophenoxy)phenoxy]propylcarbamate; $n_D^{20} = 1.5578$;

(25) p-(m-chlorophenoxy)phenol and ethyl (2-chloroethyl)methylcarbamate yield ethyl [2-[p-(m-chlorophenoxy)phenoxy]ethyl]methylcarbamate; $n_D^{20} = 1.5570$;

(26) p-(m-nitrophenoxy)phenol and ethyl 2-(methylsulphonyloxy)propylcarbamate yield ethyl 2-[p-(m-nitrophenoxy)phenoxy]propylcarbamate; $n_D^{20} = 1.5640$;

(27) p-(m-nitrophenoxy)phenol and ethyl (2-chloroethyl)methylcarbmate yield ethyl [2-[p-(m-nitrophenoxy)phenoxy]ethyl]methylcarbamate; $n_D^{20} = 1.5639$;

(28) p-(p-fluorophenoxy)phenol and ethyl 2-(methylsulphonyloxy)propylcarbamate yield ethyl 2-[p-(p-fluorophenoxy)phenoxy]propylcarbamate; m.p. 98°–100° C.;

(29) p-(o-fluorophenoxy)phenol and ethyl (2-chloroethyl)methylcarbamate yield ethyl [2-[p-(o-fluorophenoxy)phenoxy]ethyl]methylcarbamate; $n_D^{20} = 1.5399$;

(30) p-benzylphenol and ethyl 2-(methylsulphonyloxy)propylcarbamate yield ethyl 2-(p-benzylphenoxy)propylcarbamate; $n_D^{20} = 1.5538$;

(31) 4-hydroxy-benzophenone and ethyl 2-(methylsulphonyloxy)propylcarbamate yield ethyl 2-(p-benzoylphenoxy)propylcarbamate; $n_D^{20} = 1.5820$;

(32) 4-hydroxy-benzophenone and ethyl (2-chloroethyl)methylcarbamate yield ethyl [2-(p-benzoylphenoxy)ethyl]methylcarbamate; $n_D^{20} = 1.5772$;

(33) p-(p-chlorobenzyl)phenol and ethyl (2-chloroethyl)methylcarbamate yield ethyl [2-[p-(p-chlorobenzyl)phenoxy]ethyl]methylcarbamate; m.p. 56°–58° C.;

(34) p-(m-fluorophenoxy)phenol and ethyl 2-(methylsulphonyloxy)propylcarbamate yield ethyl 2-[p-(m-fluorophenoxy)phenoxy]propylcarbamate; $n_D^{20} = 1.5382$.

II. Preparation of the starting materials

EXAMPLE 2

117.2 g of 2-(n-butylamino)-ethanol are placed in 300 ml of methylene chloride. Then 54.3 g of ethyl chloroformate are allowed to drop in during 1 hour at 30°–35° C. with ice-cooling. After stirring for an additional 2 hours, the methylene chloride is evaporated and the residue is distilled to yield pure ethyl (2-hydroxyethyl)-n-butylcarbamate; b.p. 112° C./0.1 Torr.

52 g of ethyl (2-hydroxyethyl)-n-butylcarbamate are placed in 125 ml of methylene chloride and treated dropwise with 41.6 g of thionyl chloride during 45 minutes at 20°–25° C. Then the mixture is allowed to react for an additional 1 hour at room temperature. After removing the solvent, the residue is distilled to yield pure ethyl (2-chloroethyl)-n-butylcarbamate; b.p. 91° C./0.07 Torr.

In an analogous manner to that described in this Example, the following compounds are prepared:

(1) 2-isopropylamino-ethanol and ethyl chloroformate yield ethyl (2-hydroxyethyl)isopropylcarbamate of b.p. 93° C. at 0.07 Torr; and reaction with thionyl chloride yields ethyl (2-chloroethyl)isopropylcarbamate; b.p. 84° C./0.1 Torr;

(2) 2-methylamino-ethanol and methyl chloroformate yield methyl (2-hydroxyethyl)methylcarbamate of b.p. 88°–91° C./0.1 Torr; and reaction with thionyl chloride yields methyl (2-chloroethyl)methylcarbamate; b.p. 86°–90° C./0.15 Torr;

(3) 2-methylamino-ethanol and isopropyl chloroformate yield isopropyl (2-hydroxyethyl)methylcarbamate of b.p. 100° C./0.15 Torr; and reaction with thionyl chloride yields isopropyl (2-chloroethyl)methylcarbamate; b.p. 72° C./0.15 Torr;

(4) 2-methylamino-ethanol and S-ethyl chlorothioformate yield S-ethyl (2-hydroxyethyl)methylthiocarbamate of b.p. 110°–115° C./0.2 Torr; and reaction with thionyl chloride yields S-ethyl (2-chloroethyl)methylthiocarbamate; b.p. 70°–75° C./0.1 Torr;

(5) 1-amino-2-propanol and isopropyl chloroformate yield isopropyl 2-hydroxypropylcarbamate; b.p. 105°–111° C./0.65 Torr.

EXAMPLE 3

32.3 g of hydroquinone are dissolved in 250 ml of dimethyl sulphoxide. With stirring and constant introduction of nitrogen there are successively added 100 ml of toluene and 30 g of 86% potassium hydroxide. Then the bath temperature is adjusted to 160° C. and the water is completely removed by means of a water separator. Thereafter, the bath temperature is increased further and the toluene is distilled off until the internal temperature had attained 155° C. Then 40 g of 3-bromofluorobenzene are allowed to flow in and the mixture is held for 20 hours at this temperature. Thereafter, the dimethyl sulphoxide is distilled off in a water-jet vacuum. The cooled residue is poured into ice-water, made neutral with hydrochloric acid and extracted three times with ethyl acetate. The extracts are washed twice with water and once with saturated sodium chloride solution, dried over sodium sulfate and evaporated. Chromatography on silica gel with n-hexane/ethyl acetate (9:1) yields p-(m-bromophenoxy)phenol; $n_D^{20} = 1.6018$.

In an analogous manner to that described in the preceding paragraph, hydroquinone and 3-trifluoromethylchlorobenzene in the presence of a catalytic amount of copper powder yield p-($\alpha,\alpha,\alpha$-trifluoro-m-tolyloxy)-phenol which distils in the bulb-tube at 140° C./0.05 Torr; $n_D^{20} = 1.5370$.

EXAMPLE 4

29.4 g of ethyl 2-hydroxypropylcarbamate are dissolved in 27 g of triethylamine and 22.9 g of methanesulphonyl chloride are added dropwise thereto at 15°–20° C. over 1 hour while stirring. The thickening reaction mixture is stirred for 2.5 hours and then poured into ice-water. The mixture is acidified by means of 2 N hydrochloric acid and extracted three times with methylene chloride. The extracts are washed neutral with water and dried over sodium sulfate. After evaporating the solvent, there is obtained ethyl 2-(methylsulphonyloxy)propylcarbamate ($n_D^{20} = 1.4577$) which can be used without further purification.

In an analogous manner to that described above,
(1) methyl 2-hydroxypropylcarbamate and methanesulphonyl chloride yield methyl 2-(methylsulphonyloxy)propylcarbamate (m.p. 37°–40° C.) which can be used without further purification;
(2) isopropyl 2-hydroxypropylcarbamate and methanesulphonyl chloride yield isopropyl 2-(methylsulphonyloxy)propylcarbamate.

EXAMPLE 5

21.8 g of sodium hydride (55% in oil) are placed in 100 ml of absolute pyridine and treated dropwise during 1 hour with 54.1 g of m-cresol in 200 ml of pyridine. After completion of the reaction, 1.2 g of cuprous chloride are added and subsequently 93.5 g of 4bromoanisole are added dropwise during 1 hour at reflux temperature. After refluxing for 4 hours, the pyridine is distilled off, the mixture being heated at the end up to 170° C. (internal temperature). After 2 hours, 350 ml of water are added dropwise with ice-cooling, followed by 500 ml of diethyl ether and a further 150 ml of water. The mixture is filtered with suction over Celite and the phases are separated. The organic phase is washed in sequence with 200 ml of 2 N hydrochloric acid, three times with 100 ml of 2 N sodium hydroxide each time, with 200 ml of water and with 200 ml of saturated sodium chloride solution. After drying over sodium sulfate and evaporation, there is obtained a brown-red oil which is filtered over a five-fold amount of silica gel with n-hexane/diethyl ether and then distilled to yield pure p-(m-tolyloxy)anisole; b.p. 106°–108° C./0.04 Torr; $n_D^{20} = 1.5738$.

77 g of p-(m-tolyloxy)anisole are dissolved in 360 ml of acetic acid and treated with 300 ml of 48% hydrobromic acid. Then, the mixture is allowed to react at reflux temperature for 5 hours. The cooled solution is poured into 1.5 l of ice-water and extracted three times with 150 ml of methylene chloride each time. The organic solution is washed three times with 150 ml of water each time and with 150 ml of saturated sodium bicarbonate solution, dried over sodium sulfate and evaporated. Distillation of the crude product yields pure p-(m-tolyloxy)phenol; b.p. 88°–89° C./0.04 Torr.

In an analogous manner to that described above in this Example,
(1) 4-chloro-o-cresol and 4-bromoanisole yield p-(p-chloro-o-tolyloxy)anisole of b.p. 112°–116° C./0.04 Torr and reaction with hydrobromic acid/acetic acid yields p-(p-chloro-o-tolyloxy)phenol; m.p. 83°–85° C.;
(2) m-nitrophenol and bromoanisole yield p-(m-nitrophenoxy)anisole of m.p. 69°–71° C. and reaction with hydrobromic acid/acetic acid yields p-(m-nitrophenoxy)phenol which distils in the bulb-tube at 95°–97° C./0.04 Torr;
(3) 4-methoxy-o-cresol and bromobenzene yield 5-methoxy-2-phenoxytoluene of b.p. 102°–104° C./0.035 Torr and m.p. 39°–42° C. and reaction with hydrobromic acid/acetic acid yields p-phenoxy-m-cresol; m.p. 96°–99° C.;
(4) m-fluorophenol and 4-bromoanisole yield p-M-fluorophenoxy)anisole of b.p. 130°–131° C./0.2 Torr and reaction with hydrobromic acid/acetic acid yields p-(m-fluorophenoxy)phenol; m.p. 53°–55° C.

III. Formulation Examples

EXAMPLE 6

An emulsifiable concentrate appropriate for liquid compounds of formula I can contain the following ingredients:

|  | g/l |
|---|---|
| Active ingredient, a compound of formula I | 250 |
| N—Methyl-2-pyrrolidone | 300 |
| Alkylphenol-ethylene oxide adduct | 35 |
| Calcium salt of dodecylbenzene-sulphonic acid | 15 |
| Cycloalkylepoxystearate | 25 |
| Aromatic solvent (mixture of $C_{10}$—alkylbenzenes) | ad 1000 ml |

The active ingredient is dissolved in the N-methyl-2-pyrrolidone, thereafter the remaining ingredients are added and dissolved, and the mixture is made up to volume with the aromatic solvent. To prepare a ready-for-use spray liquor the present product is added to water, to spontaneously yield an emulsion (o/w) which is stable for hours.

EXAMPLE 7

A spray powder appropriate for all compounds of formula I can contain the following ingredients:

|  | Wt. % |
|---|---|
| Active ingredient, a compound of formula I | 25 |
| Silicic acid, hydrated (about 87% $SiO_2$) | 30 |
| Sodium lauryl sulphate | 2 |
| Sodium lignosulphonate | 4 |
| Kaolin, mainly $Al_2[Si_2O_5](OH)_4$ | 39 |
|  | 100 |

The active ingredient is homogeneously mixed with the remaining components in a suitable apparatus. The resulting powder is finely ground in a suitable grinding apparatus (e.g. pinned disc mill, hammer mill, ball mill or air-jet mill) to a particle size necessary for an optimum biological activity and therafter again mixed. The present spray powder is spontaneously wetted by water and gives well-suspendible, ready-for-use spray liquors.

EXAMPLE 8

A granulate appropriate for all compounds of formula I can contain the following ingredients:

|  | Wt. % |
|---|---|
| Active ingredient, a compound of formula I | 5 |
| Tetrasodium salt of ethylenediaminotetraacetic acid ($Na_4$—EDTA) | 1 |
| Pumice stone granulate 0.6–1.0 mm | 94 |
|  | 100 |

The pumice stone granulate is placed in a suitable mixing mill and an aqueous solution of the $Na_4$-EDTA is sprayed on with constant stirring. The mixture is dried at 110° C. and thereafter the active ingredient, dissolved in a suitable solvent (e.g. methylene chloride), is sprayed on the dry mixture. The solvent is evaporated by warming. There results a well-shakeable granulate which can be applied to the soil or to water by hand, with suitable granulate spreaders or even from aircraft. The porous structure of the pumice stone brings about in many cases a desirable delayed release of the active ingredient over a long time.

I claim:
1. Ethyl [2-(p-phenoxyphenoxy)ethyl]methylcarbamate.
2. S-ethyl[2-(p-phenoxyphenoxy)ethyl]methylthiocarbamate.
3. A pesticidal composition which comprises an inert carrier material and, as the active ingredient, an amount which is effective as a pesticide of a compound according to claim 1.
4. A pesticidal composition which comprises an inert carrier material and, as the active ingredient, an amount which is effective as a pesticide of a compound according to claim 2.
5. A method for the control of pests, which comprises applying to the site to be treated or the pests themselves, an amount of the compound according to claim 1 which is effective in the control of pests.
6. A method for the control pests, which comprises applying to the site to be treated or the pests themselves, an amount of the compound according to claim 2 which is effective in the control of pests.

* * * * *